United States Patent [19]

Schmierer et al.

[11] Patent Number: 4,614,535
[45] Date of Patent: Sep. 30, 1986

[54] HERBICIDAL IMIDAZOLINONES

[75] Inventors: Roland Schmierer, Gersthofen; Reinhard Handte, Gablingen; Rainer Liebl, Gersthofen; Hilmar Mildenberger, Kelkheim; Klaus Bauer, Rodgau; Hermann Bieringer, Eppstein; Helmut Bürstell, Frankfurt am Main, all of Fed. Rep. of Germany

[73] Assignee: Hoechst Aktiengesellschaft, Frankfurt am Main, Fed. Rep. of Germany

[21] Appl. No.: 669,620

[22] Filed: Nov. 8, 1984

[30] Foreign Application Priority Data

Nov. 10, 1983 [DE] Fed. Rep. of Germany ....... 3340595

[51] Int. Cl.$^4$ ............... A01N 43/50; C07D 401/02; C07D 233/70
[52] U.S. Cl. ......................... 71/92; 546/15; 546/141; 546/142; 546/144; 546/153; 546/155; 546/156; 546/157; 546/167; 546/278; 548/301
[58] Field of Search ............. 548/301; 546/278, 141, 546/142, 144, 153, 155, 156, 157, 167, 15; 71/92

[56] References Cited

U.S. PATENT DOCUMENTS 4,125,727 11/1978 Los ................................ 548/301 X
4,188,487 2/1980 Los ................................ 548/301

OTHER PUBLICATIONS

Hofmann, K., Imidazole and Its Derivatives, Part I, Interscience, New York, 1953, pp. 95-96.

Primary Examiner—Richard A. Schwartz
Attorney, Agent, or Firm—Curtis, Morris & Safford

[57] ABSTRACT

Imidazolinones of the formula

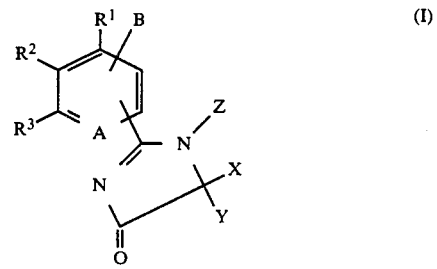

in which A denotes N or C—$R^4$; B denotes halogenoalkyl, alkoxymethyl, cyanomethyl or thiocyanatomethyl; X denotes alkyl; and Y denotes alkyl, cycloalkyl, alkenyl, phenyl or benzyl; or X and Y, together with C, denote a spiro-cycloalkyl group; Z denotes H, (substituted) alkyl, alkenyl, propargyl or an alkyl, carboxylic acid ester or sulfonic acid ester group; and $R^1$-$R^4$ denote H, halogen, alkyl, alkoxy, alkoxycarbonyl, halogenoalkyl, $NO_2$, CN, (substituted) phenoxy or (substituted) phenyl, or in each case two adjacent radicals together denote the radical —CH=CH—CH=CH—, are active herbicides and growth regulators.

5 Claims, No Drawings

HERBICIDAL IMIDAZOLINONES

The present invention relates to novel herbicidally active imidazolinones of the formula (I)

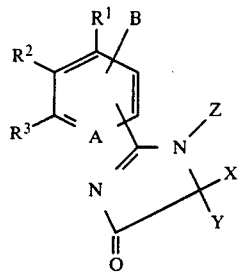

in which

A denotes N or C—$R^4$;

B denotes halogeno ($C_1$-$C_2$) alkyl, halogen being understood as meaning fluorine, chlorine or bromine, preferably fluorine or chlorine, or ($C_1$-$C_4$) alkoxymethyl, cyanomethyl or thiocyanatomethyl;

X denotes ($C_1$-$C_4$) alkyl; and

Y denotes ($C_1$-$C_6$)alkyl, cyclo ($C_3$-$C_6$) alkyl, ($C_2$-$C_4$) alkenyl, ($C_2$-$C_4$) alkinyl, phenyl or benzyl; or X and Y, together with the carbon atom to which they are bonded, denote a spirocyclo ($C_3$-$C_6$) alkyl group which is optionally substituted by —$CH_3$;

Z denotes hydrogen, ($C_1$-$C_4$) alkyl, which can be substituted by ($C_1$-$C_4$) alkoxycarbonyl, or ($C_3$-$C_4$) alkenyl, propargyl, —CO—$R^5$ or —$SO_2$—$R^6$;

$R^1$, $R^2$, $R^3$ and $R^4$ independently of one another denote hydrogen, halogen ($C_1$-$C_4$) alkyl, ($C_1$-$C_6$) alkoxy, ($C_1$-$C_6$) alkoxycarbonyl, halogeno ($C_1$-$C_2$) alkyl, nitro, cyano, phenoxy or phenyl, which can optionally be substituted by ($C_1$-$C_4$) alkyl, ($C_1$-$C_4$) alkoxy or halogen, it also being possible for in each case two radicals $R^1$, $R^2$, $R^3$ and $R^4$ in the o-position relative to one another together to form the grouping —CH=CH—CH=CH—;

$R^5$ denotes ($C_1$-$C_{12}$)alkyl, which is optionally substituted by up to two ($C_1$-$C_4$) alkoxy groups or by up to three halogen; phenyl, which can be substituted by up to two halogen or a methyl, nitro or methoxy group; or cyclo ($C_3$-$C_7$) alkyl, ($C_1$-$C_4$)alkoxy, ($C_1$-$C_4$)alkoxycarbonyl, benzyloxy, phenoxy or —$NR^7R^8$, in particular ($C_1$-$C_{12}$) alkyl;

$R^6$ denotes ($C_1$-$C_4$) alkyl, $CF_3$, $CCl_3$, phenyl, chlorophenyl or methylphenyl;

$R^7$ denotes hydrogen or ($C_1$-$C_4$) alkyl; and $R^8$ denotes ($C_1$-$C_4$) alkyl, phenyl, chlorophenyl, methylphenyl, amino or mono- or di($C_1$-$C_4$) alkylamino, and optical isomers thereof (if X≠Y), their acid addition salts and N-oxides (if A represents N).

The compounds according to the invention are obtained by cyclizing the amides of the formula (II)

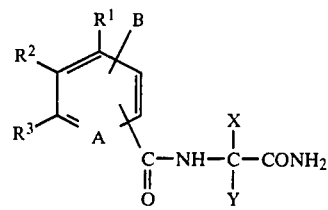

by splitting off water and, if desired, the resulting compounds where Z=hydrogen are converted into other compounds of the formula (I) by alkylation, acylation, sulfonation, oxidation or salt formation.

The cyclization of the amides (II) can be carried out, for example, with phosphorus pentachloride, advantageously in the presence of a solvent which is inert under the reaction conditions. Examples of the latter which may be mentioned are: toluene, xylene, chloroform or phosphorus oxychloride. The reaction temperature is not critical and can be varied between −10° C. and +150° C. Reaction temperatures of between 0° and 100° C. are particularly advantageous. The hydrochlorides of the imidazolinones (I) are thereby primarily obtained. The free bases can be prepared therefrom by customary methods, for example by reaction with sodium carbonate or sodium bicarbonate.

The cyclization can also be carried out in the presence of strong organic or inorganic acids, such as sulfuric acid or p-toluenesulfonic acid, with simultaneous removal of the water formed, at temperatures from 0° C. to 150° C. The reaction can be particularly advantageously carried out by a procedure in which the water formed is removed by azeotropic distillation with a solvent, such as toluene, xylene or chloroform. After neutralization, the products can be isolated by customary methods.

The imidazolinones of the formula (I) (Z=hydrogen) are thereby in general obtained in good yields. This was surprising for the halogenalkyl-substituted representatives (B=halogenoalkyl), since it rather had to be assumed that, because the arrangement of the halogenoalkyl group is sterically very favorable, the imidazolinones (I) would dissociate to the basic imidazoline nitrogen, hydrogen halide being split off. The cyclization products of the formula (I) where Z=hydrogen can be reacted with alkylating agents (methyl iodide or dimethyl sulfate) or acylating agents (such as acid chlorides) in the presence of bases or with isocyanates in a simple manner by processes which are known per se.

If z represents hydrogen, the compounds according to the invention are tautomeric, so that they can exist in one of the two forms (Ia)/(Ib) or as a mixture of (Ia) and (Ib). These isomers also occur with the derivative where Z=H.

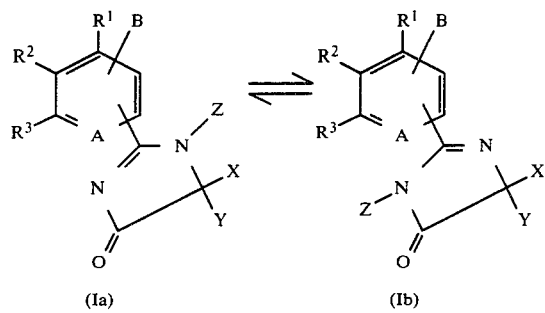

(Ia)      (Ib)

The definitions of the formula (I) always include both isomeric structures of the formulae (Ia) and (Ib).

Both the acid addition salts and the N-oxides of the compounds of the formula (I) are readily accessible by a generally known route, the latter being accessible, for example, by reaction with peroxides or $H_2O_2$.

The amides of the formula (II) can easily be obtained from the aminoamides (III) and the correspondingly substituted carboxylic acid derivatives (IV). Suitable derivatives are, for example, acid chlorides or carbonic acid alkyl esters ($R^9$=Cl or —O—COO—alkyl).

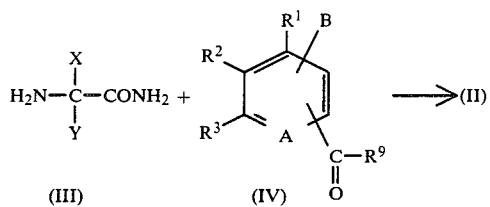

(III)      (IV)

The present compounds according to the invention exhibit an excellent herbicidal activity against a broad spectrum of economically important monocotyledonous and dicotyledonous harmful plants. The active substances also have a good action against perennial root-propagated weeds which are difficult to combat. It is irrelevant here whether the substances are applied by pre-sowing, pre-emergence or post-emergence spraying. If the compounds according to the invention are applied to the soil surface before germination, the emergence of the seedlings is not completely prevented. The weeds grow to the cotyledon stage, their growth then stops and they finally die completely after 3 weeks.

In the case of application of the active substances to the green parts of plants by the post-emergence method, a drastic stop in growth likewise occurs very rapidly after treatment, and the weeds remain in the growth stage of the time of application or die completely after a certain period, so that weed competition harmful to the crop plants can in this manner be eliminated very early and permanently by using the novel agents according to the invention. Although the compounds according to the invention exhibit an excellent herbicidal activity against monocotyledonous and dicotyledonous weeds, damage to plants of economically important crops, such as, for example, wheat, barley, rye, rice, maize, sugar beet, cotton and soya bean, is only insignificant or non-existent. The substances according to the invention thus also have an excellent selectivity in crop plants, and for these reasons are particularly suitable for combating undesirable plant growth in agricultural useful plantations.

Moreover, they have growth-regulating properties on crop plants. They have a regulating effect on metabolism endogenous to plants and can thus be used for facilitating harvesting, such as, for example, by inducing desiccation, abscission and compression of growth. They are furthermore also suitable for the general control and inhibition of undesirable vegetative growth, without thereby destroying the plants. Inhibition of vegetative growth is of great importance in many monocotyledonous and dicotyledonous crops, since lodging can thereby be reduced or completely prevented.

The present invention thus also relates to herbicidal and growth-regulating agents containing the active substance of the formula (I), in addition to customary formulation auxiliaries.

The agents according to the invention can be applied as wettable powders, emulsifiable concentrates, solutions which can be sprayed, dusting agents, dressing agents, dispersions, granules or microgranules in the usual formulations.

Wettable powders are products which are uniformly dispersible in water and which, in addition to the active substance and apart from a diluent or inert substance, if appropriate, also contain wetting agents, for example polyoxyethylated alkylphenols, polyoxyethylated fatty alcohols and alkyl- or alkylphenyl-sulfonates, and dispersing agents, for example sodium lignin-sulfonate, sodium 2,2'-dinaphthylmethane-6,6'-sulfonate, sodium dibutylnaphthalenesulfonate or sodium oleyl-methyl-tauride. They are prepared in the customary manner, for example by grinding and mixing the components.

Emulsifiable concentrates can be prepared, for example, by dissolving the active substance in an inert organic solvent, for example butanol, cyclohexanone, dimethylformamide, xylene or higher-boiling aromatics or hydrocarbons, with the addition of one or more emulsifiers. In the case of liquid active substances, all or some of the solvent content can also be dispensed with. Examples of emulsifiers which can be used are: calcium alkyl-arylsulfonates, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, fatty alcohol/propylene oxide/ethylene oxide condensation products, alkyl polyglycol ethers, sorbitan fatty acid esters, polyoxyethylene sorbitan fatty acid esters or polyoxyethylene sorbitol esters.

Dusting agents can be obtained by grinding the active substance with finely divided, solid substances, for example talc or natural clays, such as kaolin, bentonite, pyrophilite or diatomaceous earth.

Granules can be prepared either by spraying the active substances onto adsorbent granular inert material or by applying active substance concentrates to the surface of carriers, such as sand or kaolinites, or granular inert material by means of binders, for example polyvinyl alcohol, sodium polyacrylate or mineral oils. Suitable active substances can also be granulated in the usual manner for the preparation of fertilizer granules, if desired as a mixture with fertilizers.

The active substance concentration in wettable powders is, for example, about 10 to 90% by weight, the remainder to make up to 100% by weight consisting of the usual formulation constituents. The active substance concentration in emulsifiable concentrates can be about 10 to 80% by weight. Dust-like formulations usually contain 5 to 20% by weight of active substance, and solutions which can be sprayed contain about 2 to 20% by weight. The active substance content in granules depends partly on whether the active compound is in the liquid or solid form and on which granulation auxiliaries, fillers and the like are used.

The active substance formulations mentioned additionally contain, if appropriate, the particular customary tackifiers, wetting agents, dispersing agents, emulsifying agents, penetration agents, solvents, fillers or carriers.

For application, the concentrates in the commercially available form are diluted, if appropriate, in the customary manner, for example by means of water in the case of wettable powders, emulsifiable concentrates, dispersions and sometimes also microgranules. Dust-like and granular formulations and solutions which can be sprayed are not usually further diluted with additional inert substances before use.

The amounts of active substance of the formula I applied vary between 0.01 and 10 kg of active substance/ha, depending on the indication.

Mixtures or mixed formulations with other active substances, such as, for example, insecticides, acaricides, herbicides, fertilizers, growth regulators or fungicides, are also possible, where relevant.

Some formulation examples are described below:

A dusting agent is obtained by mixing 10 parts by weight of active substance and 90 parts by weight of of talc or inert substance and comminuting the mixture in an impact mill.

A powder which is readily dispersible and wettable in water is obtained by mixing 25 parts by weight of active substance, 64 parts by weight of kaolin-containing quartz, as the inert substance, 10 parts by weight of potassium lignin-sulfonate and 1 part by weight of sodium oleyl-methyl-tauride, as the wetting agent and dispersing agent, and grinding the mixture in a pinned disc mill.

A dispersion concentrate which is readily dispersible in water is obtained by mixing 20 parts by weight of active substance with 6 parts by weight of alkylphenol polyglycol ether (e.g. ®Triton X 207, a product of Rohm and Haas Co.) 3 parts by weight of isotridecanol polyglycol ether (8 moles of ethylenes oxide) and 71 parts by weight of paraffinic mineral oil (boiling range, for example, about 255° to above 377° C.), and grinding the mixture to a fineness of less than 5 microns in a ball mill.

An emulsifiable concentrate is obtained from 15 parts by weight of active substance, 75 parts by weight of cyclohexanone, as the solvent, and 10 parts by weight of oxyethylated nonylphenol (10 moles of ethylene oxide), as the emulsifier.

The following examples serve to further illustrate the invention:

A. PREPARATION EXAMPLES

Example 1

Starting substance

2-Trifluoromethylbenzoic acid N-2-(2-carbamoyl-3-methyl)-butylamide 15 g (0.072 mole) of 2-trifluoromethylbenzoyl chloride are added dropwise to a solution of 10.3 g (0.079 mole) of 2-methylvaline amide and 8.7 g (0.086 mole) of triethylamine in 50 ml of absolute methylene chloride at 0°-5° C. After a reaction time of 1 hour at room temperature, the mixture is poured onto 500 ml of 0.5N sodium bicarbonate solution and subsequently stirred and the solid is filtered off with suction. After drying, 18.3 g (85% of theory) of 2-trifluoromethylbenzoic acid N-2-(2-carbamoyl-3-methyl)-butylamide are obtained as a colorless solid of melting point 124° to 126° C.

Example 2

5-Isopropyl-5-methyl-4-oxo-2-(2-trifluoromethylphenyl)-2-imidazoline 18.3 g (0.06 mole) of 2-trifluoromethylbenzoic acid N-2-(2-carbamoyl-3-methyl)-butylamide are dissolved in 100 ml of phosphorus oxychloride, and 14.0 g (0.067 mole) of phosphorus pentachloride are added in portions at room temperature. After 5 hours at room temperature, the mixture is evaporated in vacuo, the residue is hydrolyzed with ice, the mixture is neutralized with sodium bicarbonate solution and the solution is extracted twice with 100 ml of ethyl acetate each time. After drying over sodium sulfate and evaporation, 15.5 g (91% of theory) of 5-isopropyl-5-methyl-4-oxo-2-(2-trifluoromethylphenyl)-2-imidazoline are obtained as a colorless solid of melting point 109° to 110° C.

Example 3

2-(2-Dichloromethylphenyl)-5-5-diethyl-4-oxo-1-(4-toluenesulfonyl)-2-imidazoline 3.2 g (0.017 mole) of 4-toluenesulfonyl chloride are added to 4.5 g (0.015 mole) of 2-(2-dichloromethylphenyl)-5-5-diethyl-4-oxo-2-imidazoline in 30 ml of absolute pyridine at 0°-5° C., the mixture is left to stand at room temperature for 1 day, poured onto 500 ml of water and extracted twice with 100 ml of toluene each time and the organic phase is washed once with 2N sodium hydroxide solution and once with water. After drying (sodium sulfate) and evaporation, the residue is purified by chromatography (silica gel, eluant: petroleum ether/ethyl acetate 7:3). 4.4 g (66% of theory) of 2-(2-dichloromethylphenyl)-5-diethyl-4-oxo-1-(4-toluenesulfonyl)-2-imidazoline are obtained as a colorless solid of melting point 139°-140° C.

TABLE 1

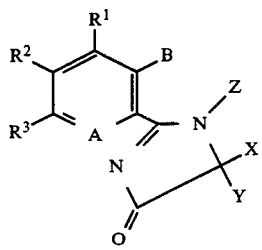

| Example | A | B | X | Y | Z |
|---|---|---|---|---|---|
| 4 | C—R⁴ | —CH₂Cl | —CH₃ | —CH(CH₃)₂ | H |
| 5 | " | " | " | " | " |
| 6 | " | —CHCl—CH₃ | " | —C₂H₅ | " |
| 7 | " | —CHCl₂ | " | —CH₃ | " |
| 8 | " | " | " | —C₂H₅ | " |
| 9 | " | " | " | —CH(CH₃)₂ | " |
| 10 | " | " | " | " | " |
| 11 | " | " | " | " | —COCH₃ |
| 12 | " | " | " | " | —CONHCH₃ |
| 13 | " | " | " | " | —COCH(CH₃)₂ |
| 14 | " | " | " | " | —CO—Phenyl |
| 15 | " | " | " | " | —SO₂—CH₃ |
| 16 | " | " | " | " | —COOC₂H₅ |
| 17 | " | " | " | " | H |
| 18 | " | " | " | " | " |
| 19 | " | " | " | " | " |
| 20 | N | " | " | " | " |
| 21 | " | " | " | " | —COCH₃ |
| 22 | C—R⁴ | " | " | —CH₂—CH(CH₃)₂ | H |
| 23 | " | " | —C₂H₅ | —C₂H₅ | " |
| 24 | " | " | —CH(CH₃)—CH₂—CH₂—CH₂—CH₂— | | " |
| 25 | " | " | —CH₃ | —CH(CH₃)₂ | " |
| 26 | N | " | " | " | " |
| 27 | C—R⁴ | —CCl₃ | " | " | " |
| 28 | " | " | " | " | CH(CH₃)COOCH₃ |
| 29 | " | " | " | " | COCOOCH₃ |
| 30 | " | " | " | Cyclopropyl | CONHN(CH₃)₂ |
| 31 | " | CHCl₂ | " | —CH(CH₃)₂ | CH₃ |
| 32 | " | " | " | " | CH₂COOCH₃ |
| 33 | " | " | " | " | CH(CH₃)COOC₂H₅ |
| 34 | " | CHOCH₃ | " | " | " |

| Example | R¹ | R² | R³ | R⁴ | Melting point (°C.) |
|---|---|---|---|---|---|
| 4 | H | H | H | H | Oil |
| 5 | " | " | " | " | 167 (hydrochloride) |
| 6 | " | " | " | " | Oil |
| 7 | " | " | " | " | 156-7 |
| 8 | " | " | " | " | 145-8 |
| 9 | " | " | " | " | 147-9 |
| 10 | " | " | " | " | 185-7 (hydrochloride) |
| 11 | " | " | " | " | Resin |
| 12 | " | " | " | " | Oil |
| 13 | " | " | " | " | " |
| 14 | " | " | " | " | " |
| 15 | " | " | " | " | Resin |
| 16 | " | " | " | " | 93 |
| 17 | " | " | Cl | " | 138-42 |
| 18 | Cl | " | " | " | 140-3 |
| 19 | H | —CHCl₂ | H | " | 135 (decomposition) |
| 20 | " | " | " | — | Oil |
| 21 | " | " | " | — | " |
| 22 | " | " | " | " | 122-3 |
| 23 | " | " | " | " | 142 |
| 24 | " | " | " | " | Oil |
| 25 | " | " | —CH=CH—CH=CH— | " | " |
| 26 | " | —CH=CH—CH=CH— | — | | " |
| 27 | " | H | H | H | 145 (decomposition) |
| 28 | | | | " | |
| 29 | | | | " | |
| 30 | | | | " | |
| 31 | | | | " | Oil |
| 32 | | | | " | " |
| 33 | | | | " | " |
| 34 | | | | " | 70-74 |

B. BIOLOGICAL EXAMPLES

Test for herbicidal action

The damage to the weeds and the tolerance by the crop plants were rated in a key from 0 to 5.

In this key:
0 = no action (damage)
1 = 0–20% action
2 = 20–40% action
3 = 40–60% action
4 = 60–80% action
5 = 80–100% action

1. Action against weeds

Seeds or pieces or rhizome of monocotyledonous and dicotyledonous weeds were placed in loam soil in plastic pots ($\phi$9 cm) and covered with soil. The compounds according to the invention, formulated as wettable powders or as emulsion concentrates, were applied to the soil surface in the form of aqueous suspensions or emulsions. The amount of water applied per pot thereby corresponded, when converted, to 600 liter/ha. After the treatment, the test pots were placed in a greenhouse and the test plants were grown under good growing conditions (temperature: 23±1° C.; relative atmospheric humidity 60–80%). After 3 weeks, the damage to the plants was rated visually. Untreated controls served as a comparison here.

As can be seen from the values in Table 2, the compounds according to the invention exhibit a herbicidal activity, which is in some cases excellent, against economically important monocotyledonous and dicotyledonous harmful plants when applied by the pre-emergence method.

In a similar manner, various weeds were grown to the 3 to 6 leaf stage in pots in a greenhouse and then treated with the compounds according to the invention (formulated as wettable powders) by the post-emergence method. 4 weeks later, the test plants were rated visually in comparison with untreated control plants by estimating the damage.

The results of the experiment (Table 3) demonstrate the good herbicidal properties of the compounds.

TABLE 2

Herbicidal activity in the pre-emergence method (% damage)

| Example No. | kg of active substance/ha | STM | CRS | SIA | LOM | ECG |
|---|---|---|---|---|---|---|
| 4 | 2.4 | 5 | 5 | 5 | 5 | 5 |
| 5 | 2.4 | 5 | 5 | 5 | 5 | 5 |
| 9 | 2.4 | 5 | 5 | 5 | 5 | 5 |
| 10 | 2.4 | 5 | 5 | 5 | 5 | 5 |
| 11 | 2.4 | 5 | 5 | 5 | 5 | 5 |
| 22 | 2.4 | | | | 4 | 4 |
| 23 | 2.4 | 4 | | 5 | 4 | |
| 27 | 2.4 | 5 | 5 | 5 | 5 | 5 |
| 34 | 2.4 | 5 | | 5 | 4 | 4 |

| | | ALM | POA | AMR | SIA | TAW | GS |
|---|---|---|---|---|---|---|---|
| 4 | 2.4 | 5 | — | 5 | 5 | — | — |
| 5 | 2.4 | 5 | — | 5 | 5 | 5 | 5 |
| 7 | 2.4 | 4 | 5 | 5 | 5 | — | — |
| 8 | 2.4 | 5 | 5 | 5 | 5 | — | — |
| 9 | 2.4 | 5 | 5 | 5 | 5 | 5 | 5 |
| 10 | 2.4 | 5 | 5 | 5 | 5 | 5 | 5 |
| 11 | 2.4 | 5 | — | 5 | 5 | 4 | 4 |
| 12 | 2.4 | 5 | 5 | 5 | 5 | 5 | 4 |
| 14 | 2.4 | 5 | 5 | 5 | 5 | 5 | 4 |
| 15 | 2.4 | 5 | — | 5 | 5 | — | — |
| 16 | 2.4 | 4 | 5 | 5 | 5 | 4 | 4 |
| 17 | 2.4 | — | — | 5 | 4 | — | — |
| 27 | 2.4 | 5 | — | 5 | 5 | 5 | 5 |
| 33 | 2.4 | 5 | 5 | 5 | 5 | 5 | 5 |

ALM = *Alopecurus myosuroides*
POA = *Poa annua*
AMR = *Amaranthus retroflexus*
TAW = *Triticum aestivum (Winter)*
GS = *Glycine soya*
STM = *Stellaria media*
CRS = *Chrysanthemum segetum*
SIA = *Sinapis alba*
LOM = *Lolium multiflorum*
ECG = *Echinochloa crus-galli*

TABLE 3

Herbicidal activity in the post-emergence method (% damage)

| Example No. | kg of active substance/ha | SIA | CRS | ECG | LOM |
|---|---|---|---|---|---|
| 4 | 2.4 | 5 | 5 | 4 | 4 |
| 5 | 2.4 | 5 | 4 | 4 | 4 |
| 9 | 2.4 | 5 | — | — | — |
| 10 | 2.4 | 4 | — | — | — |
| 11 | 2.4 | 5 | — | 4 | 4 |
| 27 | 2.4 | 5 | 5 | 4 | 4 |

| | | ALM | POA | AMR | SIA | GS |
|---|---|---|---|---|---|---|
| 4 | 2.4 | — | — | 5 | 5 | 5 |
| 5 | 2.4 | 4 | 4 | 5 | 5 | — |
| 9 | 2.4 | — | — | 5 | 5 | — |
| 11 | 2.4 | — | — | 5 | 5 | — |
| 12 | 2.4 | — | — | 5 | 5 | — |
| 14 | 2.4 | — | — | 5 | 5 | — |
| 15 | 2.4 | — | — | 5 | 5 | — |
| 16 | 2.4 | — | — | 5 | 4 | — |
| 18 | 2.4 | — | — | 5 | — | — |
| 27 | 2.4 | — | 5 | 5 | 5 | — |
| 33 | 2.4 | — | — | 5 | 5 | — |

Test for growth-regulating action

1. Inhibition of growth in cereals

In dish experiments in a greenhouse, young cereal plants (wheat, barley and rye) in the 3-leaf stage were sprayed with the compounds to be tested in the active substance concentrations stated in Table 4 (kg/ha), until dripping wet. When the untreated control plants had reached a growth height of about 55 cm, the additional growth of all the plants was measured and the inhibition of growth in % of the additional growth of the control plants was calculated. The phytotoxic action of the compounds was also observed. The results are summarized in Table 4. In the inhibition of growth data, 100% means that growth has stopped and 0% denotes a growth corresponding to that of the untreated control plants.

TABLE 4

| Compound according to Example No. | Concentration applied (kg/ha) | Inhibition in growth in % on | | | Phytotoxic action |
|---|---|---|---|---|---|
| | | wheat | barley | rye | |
| 4 | 2.5 | 29 | 31 | 25 | No damage |
| | 1.25 | 27 | 29 | 20 | |
| 10 | 2.5 | 22 | 28 | 27 | Slight damage |
| | 1.25 | 15 | 24 | 26 | |
| 27 | 2.5 | 26 | 29 | 22 | No damage |
| | 1.25 | 24 | 27 | 19 | |

2. Inhibition of growth of dwarf beans

Dwarf beans 10–15 cm high were sprayed with the active substance formulations until dripping wet. After 2 weeks, the additional growth was measured and the inhibition of growth in % of the additional growth of the control plants was calculated. The results are summarized in Table 5.

TABLE 5

| Compound according to Example No. | Concentration applied (kg/ha) | Inhibition in growth in % | Phytotoxic action |
|---|---|---|---|
| 10 | 2.5 | 41 | Slight damage |
| | 1.25 | 28 | |
| 27 | 2.5 | 39 | No damage |
| | 1.25 | 31 | |

We claim:

1. An imidazolinone of the formula I

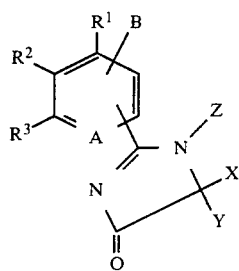

in which

A denotes N or C–$R^4$;

B denotes halogeno ($C_1$–$C_2$) alkyl, wherein halogen means fluorine, chlorine or bromine, or ($C_1$–$C_4$) alkoxymethyl, cyanomethyl or thiocyanatomethyl;

X denotes ($C_1$–$C_4$) alkyl; and

Y denotes ($C_1$–$C_6$)alkyl, cyclo ($C_3$–$C_6$) alkyl, ($C_2$–$C_4$) alkenyl, ($C_2$–$C_4$) alkinyl, phenyl or benzyl; or X and Y, together with the carbon atom to which they are bonded, denoted a spirocyclo ($C_3$–$C_6$) alkyl group which is optionally substituted by —$CH_3$;

Z denotes hydrogen, ($C_1$–$C_4$) alkyl, which can be substituted by ($C_1$–$C_4$) alkoxycarbonyl, or ($C_3$–$C_4$) alkenyl, propargyl, —CO—$R^5$ or —$SO_2$—$R^6$;

$R^1$, $R^2$, $R^3$ and $R^4$ independently of one another denote hydrogen, halogen, ($C_1$–$C_4$) alkyl, ($C_1$–$C_6$) alkoxy, ($C_1$–$C_6$) alkoxycarbonyl, halogeno ($C_1$–$C_2$) alkyl, nitro, cyano, phenoxy or phenyl, which can optionally be substituted by ($C_1$–$C_4$) alkyl, ($C_1$–$C_4$) alkoxy or halogen, it also being possible for in each case two radicals $R^1$, $R^2$, $R^3$ and $R^4$ in the o-position relative to one another together to form the grouping —CH=CH—CH=CH—;

$R^5$ denotes ($C_1$–$C_{12}$) alkyl, which is optionally substituted by up to two ($C_1$–$C_4$) alkoxy groups or by up to three halogen; phenyl, which can be substituted by up to two halogen or a methyl, nitro or methoxy group; or cyclo ($C_3$–$C_7$) alkyl, ($C_1$–$C_4$) alkoxy, ($C_1$–$C_4$)alkoxycarbonyl, benzyloxy, phenoxy or —$NR^7R^8$;

$R^6$ denotes ($C_1$–$C_4$) alkyl, $CF_3$, $CCl_3$, phenyl, chlorophenyl or methylphenyl;

$R^7$ denotes hydrogen or ($C_1$–$C_4$) alkyl; and $R^8$ denotes ($C_1$–$C_4$) alkyl, phenyl, chlorophenyl, methylphenyl, amino or mono- or di($C_1$–$C_4$) alkylamino, or an optical isomer thereof (if X≠Y), an acid addition salt or N-oxide (if A represents N).

2. The compound as claimed in claim 1, wherein halogen means fluorine or chlorine.

3. The compound as claimed in claim 1, wherein $R^5$ denotes ($C_1$–$C_{12}$) alkyl.

4. A herbicidal and plant growth-regulating agent containing an effective amount of a compound of the formula (I) as claimed in claim 1 and a carrier.

5. A method of combating undesired plants and for regulating plant growth, which comprises applying an effective amount of a compound of the formula (I) as claimed in claim 1 to an area to be treated or to the plants to be treated.

* * * * *